US008623239B2

(12) United States Patent
Tobita et al.

(10) Patent No.: US 8,623,239 B2
(45) Date of Patent: Jan. 7, 2014

(54) COMPOUND AND FUNCTIONAL LUMINESCENT PROBE COMPRISING THE SAME

(75) Inventors: Seiji Tobita, Gunma (JP); Toshitada Yoshihara, Gunma (JP); Masahiro Hosaka, Gunma (JP); Toshiyuki Takeuchi, Gunma (JP)

(73) Assignee: National University Corporation Gunma University (JP)

( * ) Notice: Subject to any disclaimer, the term of this patent is extended or adjusted under 35 U.S.C. 154(b) by 189 days.

(21) Appl. No.: 13/124,166

(22) PCT Filed: Oct. 16, 2009

(86) PCT No.: PCT/JP2009/067919
§ 371 (c)(1),
(2), (4) Date: Apr. 14, 2011

(87) PCT Pub. No.: WO2010/044465
PCT Pub. Date: Apr. 22, 2010

(65) Prior Publication Data
US 2011/0201802 A1 Aug. 18, 2011

(30) Foreign Application Priority Data
Oct. 17, 2008 (JP) ................... 2008-269005

(51) Int. Cl.
*C09K 11/00* (2006.01)
*C09K 11/87* (2006.01)
(52) U.S. Cl.
USPC ................... 252/301.16; 252/519.13
(58) Field of Classification Search
None
See application file for complete search history.

(56) References Cited

U.S. PATENT DOCUMENTS

| 5,094,958 A | 3/1992 | Klainer et al. |
| 5,462,880 A | 10/1995 | Kane et al. |
| 2003/0211454 A1 | 11/2003 | Thomas et al. |

FOREIGN PATENT DOCUMENTS

| JP | 2002501479 | 1/2002 |
| JP | 2003254909 | 9/2003 |
| JP | 2007312688 | 12/2007 |
| JP | 2008281467 | 11/2008 |
| JP | 2010044059 | 2/2010 |
| JP | 2010070494 | 4/2010 |

| WO | 95/08107 | 9/1994 |
| WO | 01/57141 A1 | 2/2001 |
| WO | 2006/024997 | 3/2006 |

OTHER PUBLICATIONS

Arora, Paramjit S., et al., "Design of Artificial Transcriptional Activators with Rigid Poly-L-proline Linkers", *J. Am. Chem. Soc.*, (2002),124: 13067-13071.
Best, Robert B., et al., "Effect of flexibility and cis residues in single-molecule FRET studies of polyproline", *PNAS*, (2007), vol. 104; No. 48; 18964-18969.
Brinas, Raymond P., et al., "Phosphorescent Oxygen Sensor with Dendritic Protection and Two-Photon Absorbing Antenna", *J. Am. Chem. Soc.*, (2005), 127: 11851-11862.
Konno, Hideo "Phosphorescent materials for Organic Light-Emitting Diodes", *The Chemical Times*, (2006), No. 1; pp. 13-14.
Lamansky, Sergey et al., "Highly Phosphorescent Bis-Cyclometalated Iridium Complexes: Synthesis, Photophysical Characterization, and Use in Organic Light Emitting Diodes", *J. Am. Chem. Soc.*, (2001), 123: 4304-4312.
Nonoyama, Matsuo "Benzo[h]quinolin-10-yl-N Indium(III) Complexes", *Bulletin of the Chemical Society of Japan*, (1974), vol. 47(3): 767-768.
Sprouse, S. et al., "Photophysical Effects of Metal-Carbon Bonds in Ortho-Metalated Complexes of Ir(III) and Rh(III)", *J. Am. Chem. Soc.*, (1984), 106: 6647-6653.
Yoshihara, Toshitada et al., "Behavior of Oxygen in Biomolecular Lipid Membrane Determined by Using Room-Temperature Phosphorescence of Iridium Complex as Probe", *Annual Meeting of Japan Society for Molecular Science; Lecture Abstract*, (2007), 2C07.
International Search Report, PCT/JP2009/067919, dated Jan. 26, 2010.
Notification of Transmittal of Translation of the International Preliminary Report and International Preliminary Report on Patentability, PCT/JP/2009/067919, dated May 17, 2011.
"Application No. PCT/JP2009067919", Supplementary European Search Report, Feb. 23, 2012.
Office Action dated Oct. 29, 2013 in related JP2010-533937 (Partial translation), 4 pages.
Negishi et al., "3 PC-098 Synthesis and Photophysical Properties of Iridium Complexes Emitting in Near-Infrared Region", 88th Spring Annual Meeting of the Chemical Society of Japan (partial translation), Mar. 2008, 2 pages.

*Primary Examiner* — Cecilia J Tsang
*Assistant Examiner* — Ronald Niebauer
(74) *Attorney, Agent, or Firm* — Kilpatrick Townsend & Stockton LLP (57) ABSTRACT

Disclosed is a compound characterized by comprising a linker, an oxygen-concentration-responsive phosphorophore which is linked to a first end of the linker, and a fluorophore which is lined to a second end of the linker. In the compound, it is preferred that the triplet level of the phosphorophore be lower than that of the fluorophore. The compound can be used as an oxygen-responsive luminescent probe.

8 Claims, 4 Drawing Sheets

FIG. 1

Fluorophore — Phosphorophore

FIG. 2

C343 — BTP

Aerated conditions (blue)   Argon atmosphere (purple)

COMPOUND AND FUNCTIONAL LUMINESCENT PROBE COMPRISING THE SAME

CROSS REFERENCE TO RELATED APPLICATIONS

This application claims the benefit of International Application No. PCT/JP2009/067919, filed Oct. 16, 2009, which claims priority to Japanese Patent Application No. 2008-269005, filed Oct. 17, 2008, which are both incorporated herein by reference in their entireties

TECHNICAL FIELD

The present invention relates to a novel compound and a functional luminescent probe comprising the same whose luminescent color changes depending on oxygen concentration.

BACKGROUND ART

Iridium (III) complexes (Non-Patent Documents 1-4) are known to be phosphorescent and are expected to be applied to the organic EL display, etc.

On the other hand, the present inventors have discovered an iridium complex ((btp)$_2$Ir(acac)) that emits oxygen concentration-dependent phosphorescence, and have developed the method for measuring oxygen concentration in biological tissues using the room-temperature phosphorescence (intensity and lifetime) of the iridium complex ((btp)$_2$Ir(acac)) (Patent Document 1). They also succeeded in determination of oxygen concentration within liposome membrane, the visualization of oxygen concentration within cancer cells, and the tumor visualization of a tumor-bearing mouse by measuring the phosphorescence intensity and lifetime of (btp)$_2$Ir(acac) (Patent Document 1).

In addition, a compound that emits phosphorescence in the near-infrared area in a oxygen concentration-dependent manner has been developed (Patent Document 2). A water soluble phosphorescent compound has also been developed (Patent Document 3).

The luminescent probe method using the iridium complex as described above is very useful to the noninvasive and super-sensitive measurement of the oxygen concentration in a specific part of a microstructure like cells. In general, the method for measuring the oxygen concentration with a luminescent probe utilizes the probe molecules whose luminescence is quenched by collisions with oxygen molecules; that is, the luminescent probe whose luminous intensity changes depending on the oxygen concentration. However, the method for determining the oxygen concentration based on the change of the luminescence intensity gave an accurate value when the concentration of the probe molecule and the excitation-light intensity distribution are uniform, while there is a problem that analysis becomes difficult because of the influence of the concentration when the concentration distribution of the probe molecule is not uniform such as the measurement of the oxygen concentration in a cell.

Therefore, a method based on the change of a luminescence lifetime is considered as a method that is not influenced by concentration, but there is such a drawback that a device becomes large-scale because an expensive light source such as a pulse laser and advanced light measurement technique are generally required for the measurement of the luminescence lifetime.

PRIOR ART DOCUMENTS

Patent Documents

Patent Document 1: Seiji Tobita, Toshitada Yoshihara, Toshiyuki Takeuchi, Masahiro Hosaka, Japanese Laid Open Patent Application No. 2008-281467.
Patent Document 2: Toshitada Yoshihara, Seiji Tobita, Masahiro Hosaka, Toshiyuki Takeuchi, Japanese Patent Application No. 2008-185151.
Patent Document 3: Toshitada Yoshihara, Seiji Tobita, Masahiro Hosaka, Toshiyuki Takeuchi, Japanese Patent Application No. 2008-239660.

Non-Patent Documents

Non-Patent Document 1: S. Lamansky, P. Djurovich, D. Murphy, F. Abdel-Razzaq, H. Lee, C. Adachi, P. E. Burrows, S. R. Forrest, and M. E. Thompson, J. Am. Chem. Soc., 123, 4303 (2001).
Non-Patent Document 2: H. Konno, Chem. Times, 199, 13 (2006).
Non-Patent Document 3: M. Nonoyama, Bull. Chem. Soc. Jpn., 47, 767 (1974).
Non-Patent Document 4: S. Sprouse, K. A. King, P. J. Spellane, and R. J. Watts, J. Am. Chem. Soc., 106, 6647 (1984).

SUMMARY OF THE INVENTION

An object of the present invention is to provide an oxygen-responsive luminescent probe that makes it possible to measure oxygen concentration conveniently without any influence of the probe concentration.

The present inventors made every effort to resolve the above object. As a result, they have succeeded in synthesizing a novel compound comprising a linker, an oxygen-concentration-responsive phosphorophore linked to a first end of the linker, and a fluorophore linked to a second end of the linker; and they have found that the luminescent color of the compound changes depending on oxygen concentration without any influence of the concentration of itself; and thereby completed the present invention.

That is, the present invention is as follows.

[1]: A compound comprising a linker, an oxygen-concentration-responsive phosphorophore which is linked to a first end of the linker, and a fluorophore which is linked to a second end of the linker.

[2]: The compound of [1], wherein the triplet level of the oxygen-concentration-responsive phosphorophore is lower than that of the fluorophore.

[3]: The compound of [1] or [2], wherein the oxygen-concentration-responsive phosphorophore is a group containing an iridium complex.

[4]: The compound of [3], wherein the iridium complex has the structure represented by the following formula (I).

[5]: The compound of [3], wherein the iridium complex has any one of the following structures (1) to (4).

[6]: The compound of any one of [1] to [5], wherein the fluorophore comprises any one of the following groups (5) to (7).

[7]: The compound of any one of [1] to [6], wherein the linker comprises the following structure (8).

[8]: The compound of any one of [1] to [6], wherein the linker is polyproline.

[9]: The compound of any one of [1] to [8], which is the following compound (9) or (13).

[10]: An oxygen-responsive luminescent probe comprising the compounds of any one of [1] to [9].

DETAILED DESCRIPTION OF THE INVENTION

The present invention is described in detail below.

Figure 1:
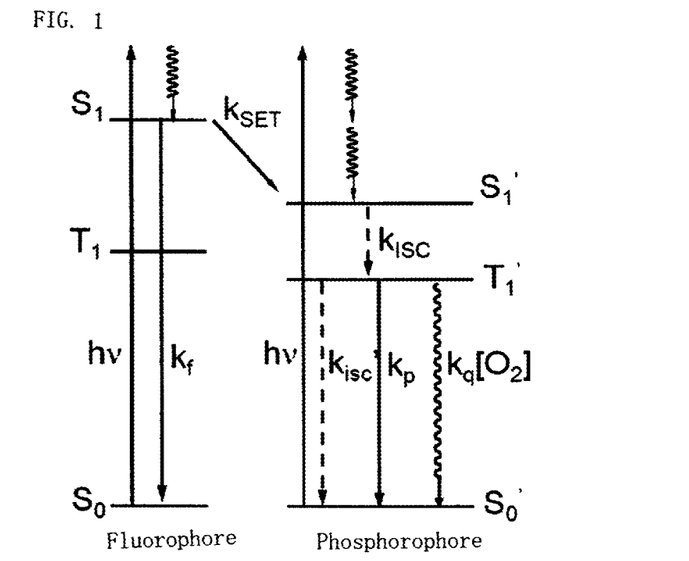
FIG. 1 shows the preferred energy relationship between the relaxation process from the excited-state of the phosphorophore and that of the fluorophore in the oxygen-responsive luminescent probe.

The compound of the present invention comprises a linker, an oxygen-responsive phosphorophore which is linked to a first end of the linker, and an oxygen-insensitive fluorophore which is linked to a second end of the linker. To design a luminescent probe whose luminescent color changes depending on oxygen concentration, as shown in FIG. 1, it is preferable to combine the luminophores so that the excited triplet (T1') of the fluorophore may be higher than that of the phosphorophore, because it is likely that the remarkably reduction of the phosphorescence intensity will be caused by energy transfer from the phosphorophore to the fluorophore when the triplet level of the fluorophore is lower than that of the phosphorophore.

It is preferable that the phosphorophore is a group comprising iridium complex; however, there is no restriction in particular, provided that the group emits phosphorescence depending on the oxygen concentration.

The iridium complex is a metal complex wherein the central metal is Ir (III) and the ligands are aromatic molecules, for example, the complexes that are disclosed in the following documents 1) to 4) are illustrated. It is preferable that the aromatic molecules as the ligands comprises heteroatoms such as nitrogen atoms, oxygen atoms, and sulfur atoms; however, there is no restriction in particular, provided that the iridium complex comprising the ligands is phosphorescent.

1) S. Lamansky, P. Djurovich, D. Murphy, F. Abdel-Razzaq, H. Lee, C. Adachi, P. E. Burrows, S. R. Forrest, and M. E. Thompson, J. Am. Chem. Soc., 123, 4303 (2001).

2) H. Konno, Chem. Times, 199, 13 (2006).

3) M. Nonoyama, Bull. Chem. Soc. Jpn., 47, 767 (1974).

4) S. Sprouse, K. A. King, P. J. Spellane, and R. J. Watts, J. Am. Chem. Soc., 106, 6647 (1984)

A preferred iridium complex includes the following:

(I)

wherein m, n, and z are integers of 0 to 3; X and Y are selected from the group consisting of hydrogen, and substituted alkyl, alkoxy, amino, dimethylamino, trifluoromethyl, cyano, acetyl, carboxyl, alkyl ester and alkyl amide groups.

A particularly preferred iridium complex includes the following:

(1)

(btp)$_2$Ir(acac)
(BTP)

(2)

(btq)$_2$Ir(acac)
(BTQ)

(3)

(btiq)₂Ir(acac)
(BTIQ)

(4)

(btph)₂Ir(acac)
(BTPH)

The excited triplet (T1') level of these phosphorophores are 198, 182, 172, and 170 kJ/mol, respectively.

The fluorophore can be properly selected on the basis of the above-described phosphorophore, including NBD (4-Nitrobenzo-2-oxa-1,3-diazole), FITC or coumarin-based dyes, rhodamines, BODIPY, a cyanine-based dyes, etc, which is preferably the following NBD, FITC, or C343:

(5)

NBD

FITC (7)

C343

The excited triplet (T1') level of these fluorophores are is 181, 197, and 206, respectively.

It is preferable that the linker that links the phosphorophore to the fluorophore is as rigid as possible to prevent the fluorophore from coming close to the phosphorophore; however, there is no restriction in particular, provided that the linker that links the phosphorophore to the fluorophore binds chemically to both of these. Moreover, the preferred length is not less than 20 Å. There is no upper limit of the length, and it is preferable not more than 30 Å. The preferred molecular weight of the linker moiety is not more than 4000.

Because steroids and polypeptides can comparatively easily link to luminophores, they can be suitably used as a linker. Moreover, the luminescent probe can be made water soluble by using a peptide including aqueous amino acids such as aspartic acid and lysine as a peptide residue. The preferred polypeptide has 4 to 20 amino acid residues, including polyproline.

For example, a compound comprising the following cholesterol skeleton can be used as the linker.

(8)

One or more carbon-carbon bond of each ring may be double bond.

More specifically, the following compounds are included. However, the compounds of the present invention include, but are not limited thereto as long as they indicate color depending on the oxygen concentration.

(9)

(10)

(11)

-continued (12)

NBD                                    decaproline (13)

C343-Pro4-BTP

BTP

Figure 2:
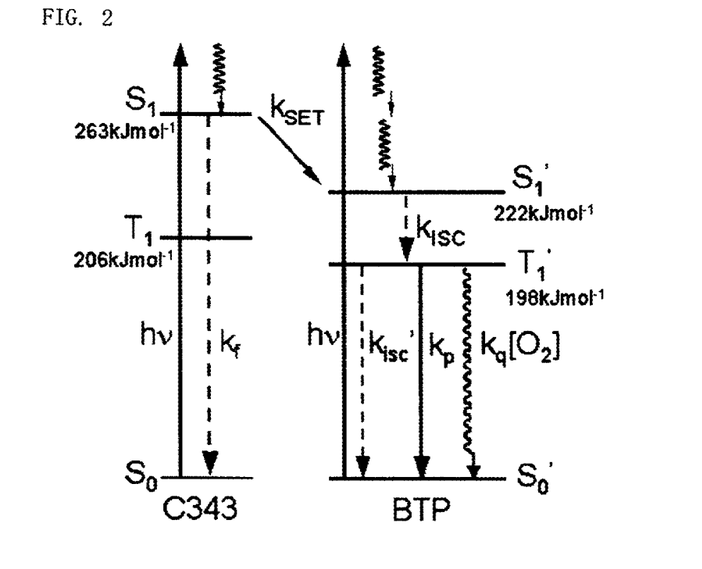
FIG. 2 shows the energy relationship in the relaxation process from the excited-state of C343-Chol-BTP.

Compound (9) satisfies the energy relationship in FIG. 1 as shown in FIG. 2.

Compound (10) and (11) also satisfy the energy relationship in FIG. 1.

Moreover, compound (13) also satisfies the energy relationship in FIG. 1.

While compound (12) does not satisfy the energy relationship in FIG. 1, even in that case, the energy transfer may be restrained and both the fluorescence and the phosphorescence can be emitted if the luminophores are linked through the long rigid linker.

The compound of the present invention can be obtained by reacting the phosphorophore compound and the fluorophore compound with a linker compound that has reactive groups at both ends. For example, the above-described compound (9) can be synthesized according to the method as described in Examples shown below. Furthermore, the following C343-Chol-BTQ, C343-Chol-BTIQ, and C343-Chol-BTPH can be obtained by replacing BTP of compound (9) with BTQ, BTIQ, or BTPH.

C343 in compound (9) can also be replaced by other fluorophores.

Figure 4:
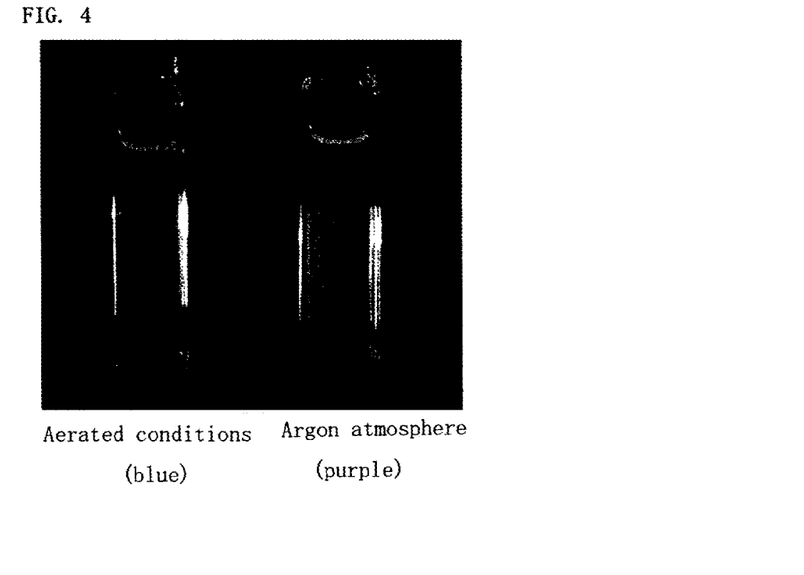
FIG. 4 shows the developed color image of C343-Chol-BTP in acetonitrile under aerated conditions and an argon atmosphere (photograph). The excitation occurred using a xenon lamp and a 430 nm band-pass filter was used.

The compound of the present invention can be used as the oxygen-responsive luminescent probe to measure the oxygen concentration based on the coloring because the luminescent color changes depending on the oxygen concentration. For example, in the case of compound (9), it can be judged that the oxygen concentration is low at purple and is high at blue (FIG. 4).

Moreover, the oxygen concentration can also be measured quantitatively by determining the relation between the oxygen concentration and the ratio of the fluorescence intensity to the phosphorescence intensity (Ip/If) beforehand.

$$\frac{I_p}{I_f} = \frac{I_p^0}{I_f} \times \frac{1}{1 + K_{SV} \times pO_2}$$

$$\frac{I_f}{I_p} = \frac{I_f}{I_p^0} \times (1 \times K_{SV} \times pO_2)$$

$K_{sv}$: Stern-Volmer constant

When detecting the oxygen concentration of a sample using the oxygen-responsive luminescent probe of the present invention, the phosphorescence can be observed by using a fluorescence microscope, a fluorescent measurement device, a fluorescent imaging device, etc., which can excite the probe, after incubation with the oxygen-responsive luminescent probe of the present invention added to the sample.

EXAMPLES

Hereinafter, the present invention is explained more specifically by referring to examples. Of course, the present invention is not limited to the following examples.

Synthesis Examples

Synthesis of (btp)$_2$Ir(sa)

To 2-Benzothienylpyridine (1175.4 mg, 3.0 mmol) and iridium chloride trihydrate (purity: 90%, 1373.6 mg, 6.5 mmol), 2-ethoxyethanol (90 ml) and H$_2$O (30 ml) were added, and the resulting mixture was refluxed for 16 hours. The solution was cooled to room temperature and the obtained solid was filtered. Dehydrated acetone (120 ml) and silver trifluoromethanesulfonate (377.2 mg, 1.47 mol) were added to the obtained solid (859 mg, 0.66 mmol), and the resulting mixture was refluxed for 3 hours and the solution was filtered. Succinylacetone (308.8 mg, 1.95 mol) and triethylamine (1 ml) were added to the obtained filtrate, followed by stirring at room temperature for 20 hours. The solution was evaporated to dryness under reduced pressure, and then the obtained solid were purified by column chromatography (eluent: chloroform:methanol (9:1, v/v))(amount: 993.5 mg and yield: 97.5%).

$^1$H HNR (300 MHz, d-DMSO, TMS, RT): δ 8.60-8.51(2H, m), 8.01-7.98(2H, d), 7.78-7.74(2H, q), 7.70-7.62(2H, q), 7.23-7.21(2H, q), 7.10-7.08(2H, q), 6.83-6.77(2H, t), 6.30-6.24(2H, t), 5.43(1H, s), 2.37-2.22(4H, m), 1.76(3H, s)

(btp)$_2$Ir(sa)

Synthesis of C343-Cho24

DMF (6 ml) was added to coumarin343 (287.8 mg, 1.0 mmol), Fmoc-ethylenediamine (345.2 mg, 1.08 mmol), and diisopropylethylamine (340 μl, 2 mmol), followed by stirring with HATU (418 mg, 1.10 mmol) as the condensing agent in an ice bath for 3 hours. H$_2$O was poured into the solution to generate a solid and the obtained solid was filtered. The obtained product was purified by column chromatography (eluent: chloroform:methanol (9:1) (amount: 380 mg and yield: 69%). 2% DBU/DMF (10 ml) solution was added to the obtained solid (380 mg, 0.69 mmol), followed by stirring at room temperature for 3 hours. H$_2$O was added to the solution, and the mixture was extracted with chloroform, followed by drying with sodium sulfate. After filtration, the filtrate was evaporated to dryness under reduced pressure. The obtained oily substance was dissolved in ethanol (10 ml), followed by stirring with 3β-hydroxy-Δ5-cholenic acid (262 mg, 0.70 mmol) and DMT-MM (415 mg, 1.5 mmol) at room temperature for 20 hours. The reaction solution was evaporated to dryness under reduced pressure and the obtained crude product was purified by column chromatography (eluent: chloroform:methanol 9:1) (amount: 280 mg, yield: 58%).

$^1$H HNR (300 MHz, CDCl$_3$, TMS, RT): δ 9.09(1H, s), 8.50 (1H, s), 6.96(1H, s), 6.89(1H, s), 5.31(1H, s), 3.62-3.58(2H, t), 3.55-3.50(2H, t), 3.34(4H, m), 2.87-2.83(2H, t), 2.78-2.74 (2H, t), 1.95(4H, m), 2.23-0.62(34H, m, cholesterol moiety)

C343-Cho24

Synthesis of C343-Chol-BTP

C343-Cho24 (101 mg, 0.148 mol), (btp)$_2$Ir(sa)(122 mg, 0.158 mol), 2-methyl-6-nitrobenzoic anhydride (MNBA, 104 mg, 0.302 mol), dimethylaminopyridine (6.5 mg, 0.053 mol), and triethylamine (65 μl, 0.46 mol) were dissolved in DMF (8 ml), followed by stirring at room temperature for 20 hours. H$_2$O was added to the reaction solution, and the mixture was extracted with ethyl acetate, followed by drying with sodium sulfate. After filtration, the filtrate was evaporated to dryness under reduced pressure. The obtained solid was purified by column chromatography (eluent: chloroform) (amount: 85.5 mg, yield: 41%).

$^1$H HNR (300 MHz, CDCl$_3$, TMS, RT): δ 9.1(1H, s), 8.58 (1H, s), 8.39(2H, d), 7.75(2H, q), 7.64-7.62(4H, d), 7.05-6.95 (5H, m), 6.79(2H, d), 6.55(1H, s), 6.25-6.15(2H, m), 5.29 (2H, s), 3.65-3.55(2H, m), 3.48-3.42(2H, m), 3.33(4H, m), 2.89(2H, t), 2.77(2H, t), 2.31-2.16(4H, m), 1.97(4H, m), 1.79 (3H, s), 2.23-0.62(34H, m, cholesterol moiety)

C343-Chol-BTP

Example 1

Emission Spectrum of C343-Chol-BTP

Figure 3:
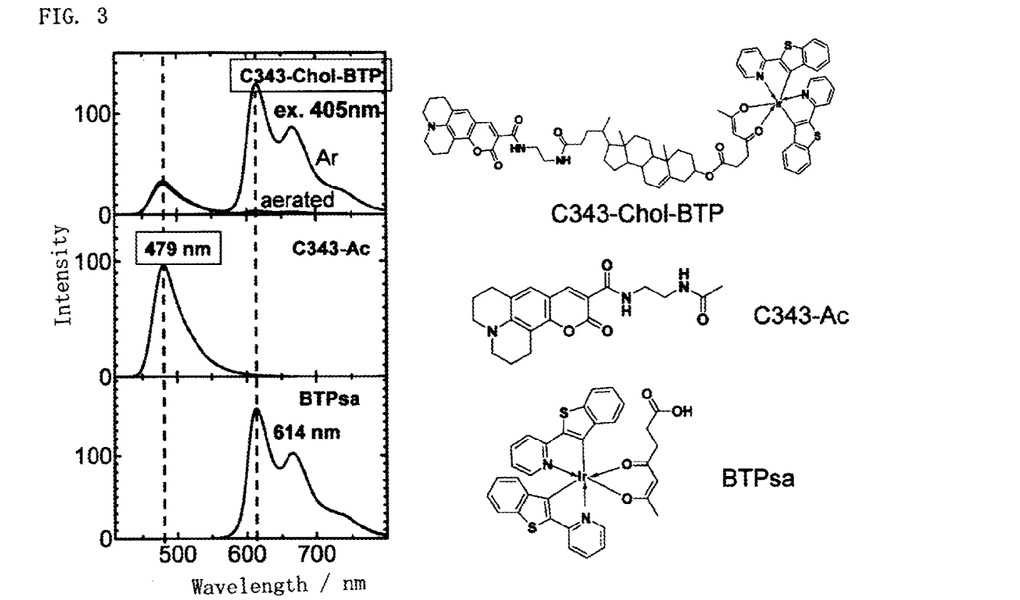
FIG. 3 shows the emission spectrum of C343-Chol-BTP in acetonitrile.

As shown in FIG. 3, the emission spectra of C343-Chol-BTP consist of the fluorescence of C343 and the phosphorescence of BTP. Both of the fluorescence and the phosphorescence were recognized under an argon (Ar) atmosphere where there is no oxygen, while the fluorescence was observed but the phosphorescence was quenched under aerated conditions. The oxygen concentration can be determined from the ratio of the fluorescence intensity to the phosphorescence intensity. FIG. 4 shows the luminescence image of C343-Chol-BTP (concentration 10.7 μM) in acetonitrile under aerated conditions and an Ar atmosphere. As a result, it was found that C343-Chol-BTP turned blue under aerated conditions, but turned purple under an Ar atmosphere.

Figure 5:
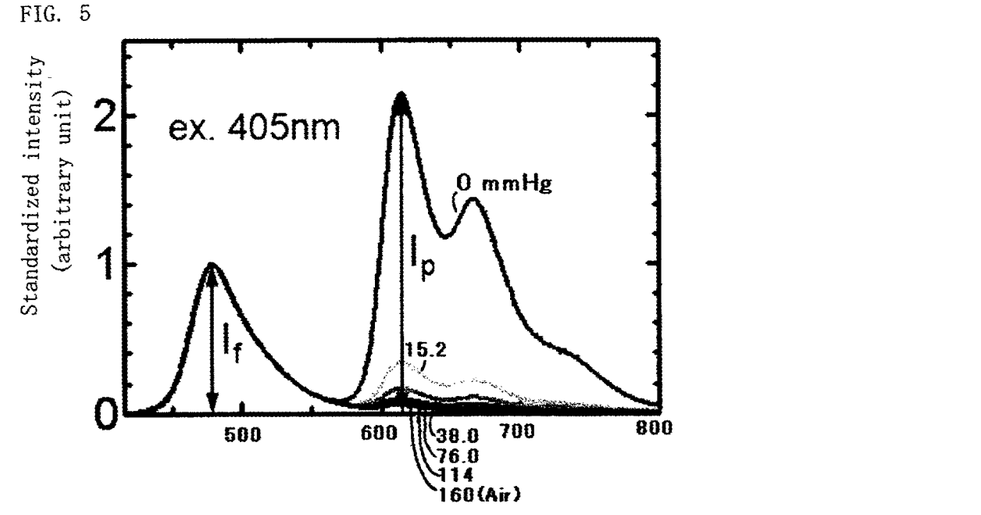
FIG. 5 shows the emission spectra of C343-Chol-BTP in acetonitrile measured at the various partial pressures of dissolved oxygen.

FIG. 5 shows the emission spectra of C343-Chol-BTP (concentration 5.7 μM) in acetonitrile measured at the various partial pressures of dissolved oxygen. It was found that the phosphorescence was quenched with increasing partial pressure of oxygen.

Figure 6:
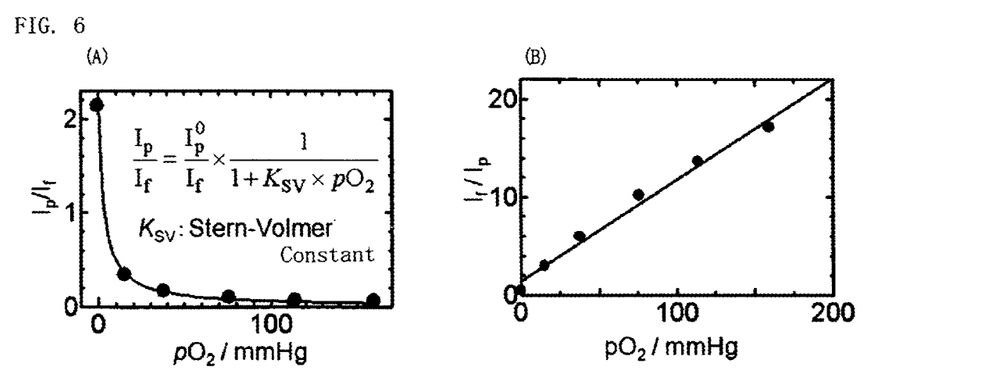
FIG. 6 shows the result of plotting the ratio of the fluorescence intensity (If) monitored at 479 nm to the phosphorescence intensity (Ip) monitored at 614 nm of C343-Chol-BTP in acetonitrile, with respect to the partial pressure of oxygen.

FIG. 6 shows the result of plotting the ratio of the fluorescence intensity monitored at 479 nm to the phosphorescence intensity monitored at 614 nm of C343-Chol-BTP (concentration 5.7 μM) in acetonitrile, with respect to the partial pressure of oxygen. According to the analysis based on the Stern-Volmer formula, it was found that the partial pressure of oxygen in the solution can be measured by measuring the ratio of the fluorescence intensity to the phosphorescence intensity.

Reference Example 1

Synthesis of Bis[2-(2'-benzothienyl)-quinolinato-N,$C^{3'}$] iridium(acetylacetone)((btq)$_2$Ir(acac))

Synthesis of 2-Benzothienylquinoline

Benzo[b]thiophene-2-ylboronic acid (990 mg, 5.6 mmol) and 2-chloroquinoline (937 mg, 5.7 mmol) were dissolved in toluene (20 ml) and ethanol (10 ml), and palladium catalyst (200 mg, 0.17 mmol) and 2M sodium carbonate solution (20 ml) were added thereto, followed by refluxing under a $N_2$ atmosphere for 5 hours. The reaction solution was added to $H_2O$ and the mixture was extracted with chloroform, followed by drying with sodium sulfate. After filtration, the filtrate was evaporated to dryness under reduced pressure. The obtained solid was washed with toluene (amount: 888 mg, yield: 61%).

$^1$H HNR (300 MHz, CDCl$_3$, TMS, RT): δ 8.20-8.17(1H, d), 8.15-8.12(1H, d), 7.98(1H, S), 7.96-7.93(1H, d), 7.91-7.88(1H, q), 7.86-7.83(1H, q), 7.82-7.79(1H, d), 7.75-7.70(1H, t), 7.55-7.50(1H, t), 7.39-7.36(2H, q)

Synthesis of Bis[2-(2'-benzothienyl)-quinolinato-N,$C^{3'}$] iridium(acetylacetone)

2-ethoxyethanol (30 ml) and H$_2$O(10 ml) were added to 2-Benzothienylquinoline (581 mg, 2.2 mmol) and iridium chloride trihydrate (purity: 90%, 392 mg, 1.0 mmol), followed by refluxing for 16 hours. The solution was cooled to room temperature and the obtained solid was filtered. To the obtained solid (304 mg, 0.20 mmol), 2-methoxyethanol (25 ml), acetylacetone (1 ml) and sodium carbonate (170 mg) were added, and the resulting mixture was refluxed for 2 hours. The solution was cooled to room temperature and the obtained solid was filtered. The obtained solid was purified by column chromatography (eluent: chloroform) (amount: 262 mg, yield: 79%).

$^1$H HNR (300 MHz, CDCl$_3$, TMS, RT): δ 8.17-8.14(2H, d), 8.01-7.98(2H, d), 7.85-7.83(2H, d), 7.75-7.73(2H, d), 7.71-7.68(2H, d), 7.37-7.32(2H, t), 7.73-7.23(2H, t), 7.02-6.97(2H, t), 6.57-6.52(2H, t), 6.32-6.30(2H, d), 4.63(1H, s), 1.55(6H, s)

(btq)₂Ir(acac)

Reference Example 2

Synthesis of Bis[1-(2'-benzothienyl)-quinolinato-N,C³'] iridium(acetylacetone)((btiq)₂Ir(acac))

Synthesis of 1-Benzothienylisoquinoline

Benzo[b]thiophene-2-ylboronic acid (997 mg, 5.6 mmol) and 1-chloroisoquinoline (946 mg, 5.8 mmol) were dissolved in toluene (20 ml) and ethanol (10 ml), and palladium catalyst (220 mg, 0.19 mmol) and 2M sodium carbonate solution (20 ml) were added thereto, followed by refluxing under a $N_2$ atmosphere for 5 hours. The reaction solution was added to $H_2O$, and the mixture was extracted with chloroform, followed by drying with sodium sulfate. After filtration, the filtrate was evaporated to dryness under reduced pressure. The obtained solid was purified by column chromatography (eluent: chloroform) (amount: 1.16 g, yield: 79%).

¹H HNR (300 MHz, CDCl₃, TMS, RT): δ 8.62-8.60(2H, d), 7.96-7.87(3H, m), 7.84(1H, s), 7.78-7.73(1H, d), 7.71-7.67(1H, d), 7.65-7.63(1H, d), 7.42-7.39(2H, m)

Synthesis of Bis[142'-benzothienyl)-quinolinato-N,C³'] iridium(acetylacetone)

2-Ethoxyethanol (30 ml) and $H_2O$ (10 ml) were added to 1-benzothienylisoquinoline (574 mg, 2.2 mmol) and iridium chloride trihydrate (purity: 90%, 398 mg, 1.0 mmol), followed by refluxing for 16 hours. The solution was cooled to room temperature and the obtained solid was filtered. To the obtained solid (250 mg, 0.17 mmol), 2-methoxyethanol (1 ml), acetylacetone (30 ml), and sodium carbonate (150 mg) were added, and the resulting mixture was refluxed. The solution was cooled to room temperature and the obtained solid was filtered. The obtained solid was purified by column chromatography (eluent: chloroform) (amount: 50 mg, yield: 18%).

¹H HNR (300 MHz, CDCl₃, TMS, RT): δ 8.92-8.88(2H, d), 8.22-8.19(2H, d), 7.88-7.84(2H, m), 7.68-7.64(4H, m), 7.56-7.54(2H, d), 7.32-7.27(2H, m), 6.94-6.91(2H, d), 6.56-6.53(2H, m), 6.18-6.14(2H, d), 5.12(1H, s), 1.63(6H, s)

(btiq)₂Ir(acac)

Reference Example 3

Synthesis of Bis[9-(2'-benzothienyl)-phenanthrinato-N, C³']iridium(acetylacetone)((btph)₂Ir(acac))

Synthesis of 9-chlorophenanthridine

Phosphorus oxychloride (15 ml) and dimethylaniline (0.63 ml) were added to phenanthridine (2.0 g), followed by refluxing for 3 hours. The solution was poured into H₂O to generate a solid, and the obtained solid was extracted with chloroform, followed by drying with sodium sulfate. After filtration, the filtrate was evaporated to dryness under reduced pressure. The obtained solid was purified by column chromatography (eluent: chloroform) (amount: 2.1 g, yield: 96%).

¹H HNR (300 MHz, CDCl₃, TMS, RT): δ 8.63-8.60(1H, d), 8.55-8.52(1H, d), 8.50-8.48(1H, d), 8.11-8.09(1H, d), 7.94-7.92(1H, t), 7.79-7.66(3H, m)

Synthesis of 9-Benzothienylphenanthridine

Benzo[b]thiophene-2-ylboronic acid (884 mg, 5.0 mmol) and 9-chlorophenanthridin (1.0 g, 4.8 mmol) were dissolved in tetrahydrofuran (30 ml), and palladium catalyst (160 mg, 0.14 mmol) and 2M sodium carbonate solution (20 ml) were added, followed by refluxing under a N₂ atmosphere for 5 hours. The reaction solution was added to H₂O and the mixture was extracted with chloroform, followed by drying with sodium sulfate. After filtration, the filtrate was evaporated to dryness under reduced pressure. The obtained solid was purified by column chromatography (eluent: chloroform) (amount: 1.15 g, yield: 78%).

¹H HNR (300 MHz, CDCl₃, TMS, RT): δ 8.74-8.71(1H, d), 8.67-8.65(1H, d), 8.62-8.59(1H), 8.26-8.23(1H, d), 7.97-7.88(3H, m), 7.86(1H, s), 7.80-7.67(3H, m), 7.44-7.41(2H)

Synthesis of Bis[9-(2'-benzothienyl)-phenanthrinato-N, C³']iridium(acetylacetone)

2-ethoxyethanol (30 ml) and H₂O (10 ml) were added to 9-benzothienylphenanthridine (706 mg, 2.3 mmol) and iridium chloride trihydrate (purity: 90%, 398 mg, 1.0 mmol), followed by refluxing for 16 hours. The solution was cooled to room temperature and the obtained solid was filtered. 2-methoxyethanol (20 ml), acetylacetone (1 ml), and sodium carbonate (180 mg) were added to the obtained solid (343 mg, 0.20 mmol), followed by refluxing for 2 hours. The solution was cooled to room temperature and the obtained solid was filtered. The obtained solid was purified by column chromatography (eluent: chloroform) (amount: 293 mg, yield: 80%).

¹H HNR (300 MHz, CDCl₃, TMS, RT): δ 9.35-9.33(2H, d), 8.72-8.70(2H, d), 8.46-8.44(2H, d), 7.98-7.87(4H, m), 7.85-7.82(2H, d), 7.73-7.70(2H, d), 7.43-7.38(2H, t), 7.20-7.15(2H, t), 7.04-6.99(2H, m), 6.52-6.51(4H, d), 4.50(1H, s), 1.39(6H, s)

Table 1 shows the phosphorescence spectra of (btq)$_2$Ir(acac), (btiq)$_2$Ir(acac), and (btph)$_2$Ir(acac) in 1,2-dichloroethane. Moreover, the phosphorescence of these compounds was dependent on the oxygen concentration (the data is not shown).

TABLE 1

The spectrum properties and the phosphorescence quantum yields of each iridium complexes in 1,2-dichloroethane

| Compound | Maximum absorption wavelength $\lambda_{abs}$/nm | Molecular extinction coefficient at the maximum absorption wavelength $\epsilon$/dm$^3$mol$^{-1}$cm$^{-1}$ | Maximum phosphorescence wavelength $\lambda_p$/nm | Phosphorescence quantum yield $\Phi_p$ |
|---|---|---|---|---|
| (btq)$_2$Ir(acac) | 540 | 8200 | 673 | 0.38 |
| (btiq)$_2$Ir(acac) | 542 | 10500 | 710 | 0.12 |
| (btph)$_2$Ir(acac) | 560 | 11700 | 719 | 0.29 |

(btq)$_2$Ir(sa), (btiq)$_2$Ir(sa), and (btph)$_2$Ir(sa), respectively, can be obtained by using succinylacetone instead of the acetylacetone in Reference Examples 1, 2, and 3. And C343-Chol-BTQ, C343-Chol-BTIQ, and C343-Chol-BTPH can be obtained by using (btq)$_2$Ir(sa), (btiq)$_2$Ir(sa) or (btph)$_2$Ir(sa) instead of (btp)$_2$Ir(acac) in the Synthesis Examples.

The following compound having T1'>T1 was synthesized and the spectrum thereof was measured, and it was found that the phosphorescence of BTP was extremely weak as compared to the fluorescence.

Example 2

Synthesis of C343-Pro-4-BTP

C343-Pro-4-BTP was synthesized by linking BTP with C343 through a tetra-proline linker according to the following step:

-continued

C343-Pro4-BTP

The emission spectrum of C343-Pro-4-BTP

Figure 7:
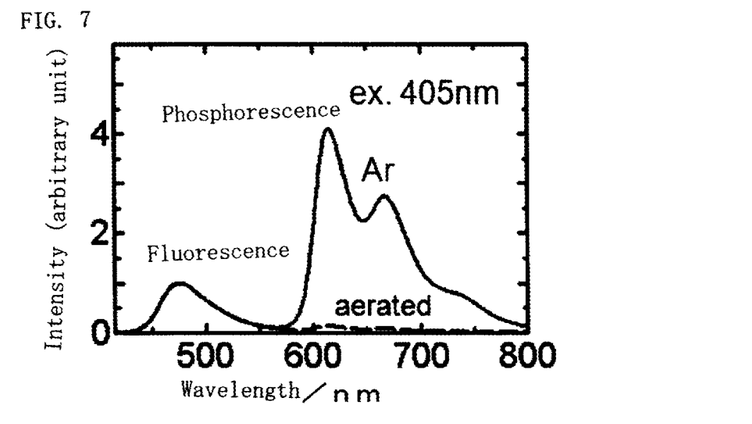
FIG. 7 shows the emission spectra of C343-Pro-4-BTP in acetonitrile under aerated conditions and an argon atmosphere (Ar).

FIG. 7 shows the emission spectrum of C343-Chol-BTP (concentration 1 μM) acetonitrile measured under aerated condition and an argon atmosphere. It was found that the phosphorescence is observed under an argon atmosphere but is quenched under aerated conditions.

Figure 8:
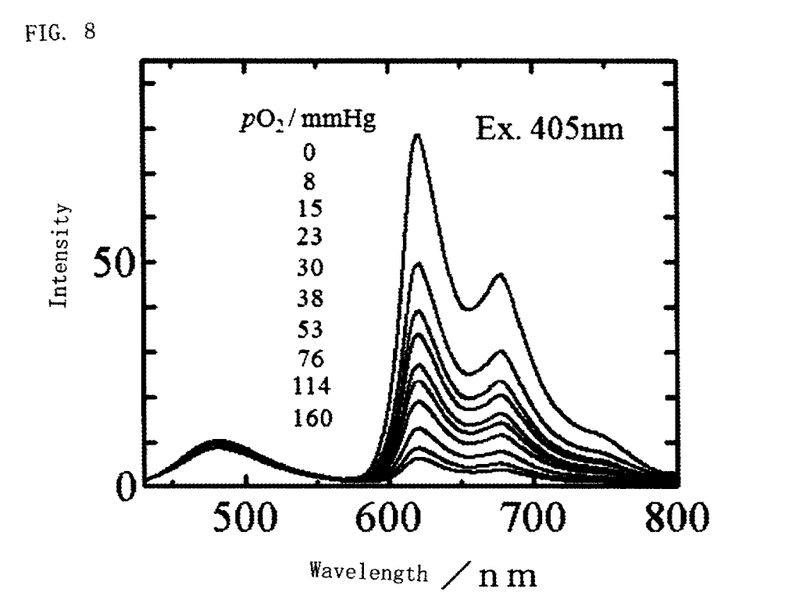
FIG. 8 shows the emission spectra of C343-Pro-4-BTP in DMPC (dimyristoyl phosphatidylcholine) lipid bilayers measured at the various partial pressures of dissolved oxygen.

FIG. 8 shows the emission spectra of C343-Pro-4-BTP (concentration: 1 μM) measured at the various partial pressures of dissolved oxygen in DMPC lipid bilayers (liposome) that were prepared by adding 1 mM of DMPC in Tris-HCl:EtOH (95:5). It was found that the phosphorescence was quenched with increasing partial pressure of oxygen.

It is considered that this probe is incorporated into cell membrane or organelle membrane because it shows lipophilicity but does not show aggregability in the liposome. Therefore, it was considered that the probe was effective for the measurement of oxygen concentration within cells.

Figure 9:
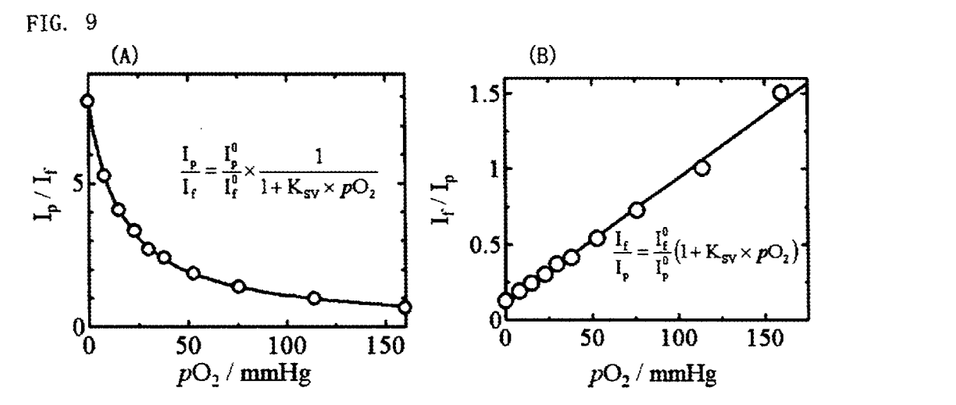
FIG. 9 shows the result of plotting the ratio of the fluorescence intensity (If) monitored at 479 nm to the phosphorescence intensity (Ip) monitored at 614 nm of C343-Pro-4-BTP in DMPC lipid bilayers, with respect to the partial pressure of oxygen.

FIG. 9 shows the result of plotting the ratio of the fluorescence intensity monitored at 479 nm to the phosphorescence intensity monitored at 614 nm of the above described C343-Pro-4-BTP (concentration: 1 μM) in DMPC lipid bilayers (liposome), with respect to the partial pressure of oxygen. According to the analysis based on the Stern-Volmer formula, it was found that the partial pressure of oxygen in the solution can be measured by measuring the ratio of the fluorescence intensity to the phosphorescence intensity.

INDUSTRIAL APPLICABILITY

The oxygen-responsive luminescent probe of the present invention is characterized by having the fluorophore which is short-lifetime fluorescent (nanosecond order) and the phosphorophore which is long-lifetime phosphorescent (microsecond order) within one molecule. The fluorescence is hardly influenced by the dissolved oxygen because of short lifetime. On the other hand, the remarkable quenching is caused by collisions with the oxygen molecule during the excitation lifetime because the phosphorescence has long lifetime. Therefore, for example, using molecules which give green luminescence to fluorophore and give red luminescence to phosphorophore makes the luminescent probe intelligent, which probe gives yellow luminescence in the absence of oxygen because of mixing luminescences of both luminophores and gives green luminescence in the existence of oxygen because of quenching the red phosphorescence. In addition, when measuring emission spectrum by using this probe, the oxygen concentration can be simply and very exactly measured according to the ratio method based on the ratio of fluorescent intensity to phosphorescence intensity.

As a result, the oxygen-responsive luminescent probe of the present invention can be used in fields such as analytical chemistry, life sciences, bioimaging, medical diagnosis, cell biology, environmental monitoring, etc. To be specific, the oxygen-responsive luminescent probe of the present invention can be used as an oxygen concentration determining reagent, a hypoxic cells imaging reagent, a tumor hypoxia diagnosing reagent, etc.

The invention claimed is:

1. A compound comprising a linker, a phosphorophore linked to a first end of the linker, and a fluorophore linked to a second end of the linker, wherein the phosphorophore is a group containing an iridium complex having any one of the following structures:

and wherein the fluorophore comprises any one of the following groups:

2. The compound of claim 1, wherein the linker comprises the following structure:

wherein one or more of carbon-carbon bonds in each ring is optionally carbon-carbon double bond.

3. The compound of claim 1, wherein the linker is polyproline.

4. An oxygen-responsive luminescent probe comprising the compound of claim 1.

5. The compound of claim 1, which is any one of the following compounds:

6. An oxygen-responsive luminescent probe comprising the compound of claim 5.

7. A compound, which is any one of the following compounds:

8. An oxygen-responsive luminescent probe comprising the compound of claim 7.

* * * * *